(12) United States Patent
Gross et al.

(10) Patent No.: US 10,688,805 B1
(45) Date of Patent: Jun. 23, 2020

(54) 3D COLORED DOT PRINTING APPARATUS AND METHOD FOR COLOR CODING

(71) Applicants: Renato Kurt Gross, Auburn, AL (US); Farrell E. Robinson, Vestavia, AL (US)

(72) Inventors: Renato Kurt Gross, Auburn, AL (US); Farrell E. Robinson, Vestavia, AL (US)

(*) Notice: Subject to any disclaimer, the term of this patent is extended or adjusted under 35 U.S.C. 154(b) by 0 days.

(21) Appl. No.: 16/115,203

(22) Filed: Aug. 28, 2018

(51) Int. Cl.
| | |
|---|---|
| *B41J 3/407* | (2006.01) |
| *B41J 2/21* | (2006.01) |
| *B41M 5/00* | (2006.01) |
| *C09D 11/03* | (2014.01) |
| *C09D 11/037* | (2014.01) |
| *C09D 11/102* | (2014.01) |

(52) U.S. Cl.
CPC ......... *B41J 2/2103* (2013.01); *B41J 3/4073* (2013.01); *B41M 5/0047* (2013.01); *B41M 5/0058* (2013.01); *B41M 5/0088* (2013.01); *C09D 11/03* (2013.01); *C09D 11/037* (2013.01); *C09D 11/102* (2013.01)

(58) Field of Classification Search
CPC ...... B41J 2/2103; B41J 2/2114; B41J 3/4073; B41J 11/0015; C09D 11/037; C09D 11/03; C09D 11/102; B41M 5/0011; B41M 5/0017; B41M 5/0088; B41M 5/0047; B41M 5/0058
See application file for complete search history.

(56) References Cited

U.S. PATENT DOCUMENTS

| | | | | |
|---|---|---|---|---|
| 2002/0067400 | A1* | 6/2002 | Kawase | B41J 2/15 347/101 |
| 2004/0253556 | A1* | 12/2004 | Iwai | G03C 7/39208 430/541 |
| 2012/0285342 | A1* | 11/2012 | Adelman | B41C 1/045 101/401 |
| 2019/0292391 | A1* | 9/2019 | Seguchi | C09D 11/322 |

* cited by examiner

*Primary Examiner* — Scott A Richmond
(74) *Attorney, Agent, or Firm* — Lanier Ford Shaver & Payne PC; Gerald M. Walsh

(57) ABSTRACT

An automated method for depositing colored thermoset resin dots on a metal surface for color coding metal surfaces, such as surfaces on surgical instruments. A liquid one component heat curing thermoset resin is combined with a colored pigment to form a colored liquid thermoset resin. A metal surface is pretreated by spraying with a surface activating agent. Thereafter, one or more drops of the colored thermoset resin are dispensed onto the surface and then heat cured (hardened), thereby forming colored thermoset resin dots. A chemical bond is formed between the colored thermoset resin and the metal, thereby making the thermoset resin dots adhere strongly and permanently to the surface. The method is fully automated with a 3-D colored dot printer and spray dispenser. The colored thermoset resin dots will not flake, peel, or turn up at the edges, thus making them useful for coding surgical instruments. The method does not require any special skill or training.

3 Claims, 6 Drawing Sheets

3D COLORED DOT PRINTING APPARATUS AND METHOD FOR COLOR CODING

FIELD OF THE INVENTION

The present invention relates to color coding instruments and, more particularly, to color coding surgical instruments with a thermoset resin in a dot form which is permanently fixed to a surface of the instrument.

BACKGROUND OF THE INVENTION

Current methods for applying a resilient colored material to a stainless steel surface, such as on a surgical instrument, require labor intensive special techniques. These methods include dipping the instrument into paint, drilling and inserting colored plugs into the surface, and applying paint by hand to the surface. A colored thermoset resin or epoxy glue dot will not adhere adequately to a stainless steel surface and cannot be used by itself to color code a stainless steel surface. Thermoset resins are used with colored ribbons which are difficult to apply. These ways of color-coding are not being adopted due to cost, not being practical, or compromising the use of the surgical instrument. A current standard of practice for color coding surgical instruments is the use of colored tape or ribbons on instruments, sometimes up to four different colors. However, the simple methods that can be used by medical personnel cause the colored materials to crack and peel which is unacceptable. Fragments of tape or ribbon on a surgical instrument can fall into a patient's cavity and edges of tape or ribbon that have lifted from the surface can harbor bacteria.

Hundreds of surgical instruments may be used in a surgical procedure with multiple surgical trays and need to go through a decontamination procedure after use. The process of sorting the instruments once they have been cleaned is a monumental task and made more difficult because the instruments are being used for multiple surgeries performed on the same day. Highly trained and experienced personnel are required to properly identify and sort the surgical instruments which is expensive, inefficient and difficult to maintain. The sterile processing departments in hospitals and clinics experience high turnover in their personnel. Time is of the essence in surgical procedures. Time spent looking for an instrument or calling down to a sterile processing department for an instrument that was supposed to be in a surgical instrument set, causes delays. The more time that a patient is under anesthesia, increases the frustration of the surgeon and staff, and increases the chance of errors in the surgical procedures.

Color coding on surgical instruments needs to be permanent, not harbor bacteria, and not compromise the function for which the instrument was intended. What is needed is an apparatus and method that will allow medical personnel to permanently, safely, and effectively color code surgical instruments with a colored thermoset resin dot, wherein the method and apparatus do not require any special skills or training.

SUMMARY OF THE INVENTION

This invention is a 3-D colored dot printing apparatus for color coding that has a track which moves a dispensing head system horizontally and vertically in X and Z directions, respectively, and a support table for one or more workpieces which moves in a horizontal Y direction, perpendicular to the X direction. The dispensing head has a surface activator dispensing head and a colored compound dispensing head. A programmable processor/controller drives the dispensing head system and activates the surface activator dispensing head and the colored compound dispensing head to deposit and bond a dot of colored thermoset resin to a metal surface of an instrument. A surface activating agent within the surface activator dispensing head is, preferably, gamma-glycidopropyltrimethoxysilane. Colored compound within the colored compound dispensing head is, preferably, a one component, heat curing, bis-phenol A thermoset resin with a colored pigment added thereto. An air pressure source is used to operate the surface activator dispensing head and the colored compound dispensing head. The colored compound dispensing head can have one or more microactuators to raise and lower the colored compound dispensing head in the Z direction and a height sensor to position the colored compound dispensing head above the metal surface of the instrument. The apparatus can also have a heat source to cure the colored dot bonding to the metal surface of the instrument.

This invention provides a mixture of a thermoset resin and a colored pigment, comprising 1% to 3% colored pigment, w/w, w/v, or v/v in a liquid one component thermoset resin, wherein the thermoset resin is, preferably, a heat curing bis-phenol A resin and wherein the thermoset resin is chemically bonded to a metal surface consisting of, preferably, iron.

This invention also provides a method of depositing colored thermoset resin dots on a metal surface for color coding. A liquid one component thermoset resin is combined with a colored pigment to form a 1% to 3% concentration of the colored pigment in the liquid one component thermoset resin, w/w, w/v, v/v, thereby forming a colored liquid thermoset compound. The liquid one component thermoset resin is, preferably, a heat curing, bis-phenol A adhesive. The metal surface is treated with a surface activating agent which is, preferably, gamma-glycidopropyltrimethoxysilane. The surface activating agent is flash evaporated from the metal surface, thereby forming an activated metal surface. The colored liquid thermoset resin is deposited on the activated metal surface and is cured by heating the colored liquid thermoset resin. This method is quickly and easily performed by the apparatus of this invention and can be operated by the end user (caregivers) producing repeatable and reliable results.

There are several advantages to this invention. The colored dot printing apparatus can hold a plurality of instruments using a magnetic and/or mechanical instrument holding system. A laser alignment device can be used with the apparatus for aiding proper manual placement and alignment of an instrument. The apparatus has full 3-D motion control for easy instrument loading and precise, repeatable, colored thermoset resin dot placement. Dispensing a surface activator on the surface of the instrument prior to placing the thermoset resin dot on the surface allows the thermoset resin to bond chemically with the metal surface. This chemical bonding makes a strong, permanent chemical adhesion of the thermoset resin dot on the surface. The processor/controller allows for complete automation of the method and requires only a single command to start and complete the process of depositing a plurality of colored thermoset resin dots in sequence on a metal surface.

Color coding metal surfaces, such as metal surgical instruments, is a simple, fast, orderly way to provide immediate recognition of surgical instruments. Personnel with little experience and training can organize surgical instruments for placement in the correct surgical set. Preferably, for example, four or more colored thermoset resin dots in a row can form a defined code, depending on the sequence of colors. The colored dots are easily visible and distinguishable. Ownership of a surgical instrument is vividly displayed for the surgeons, operating room staff, and sterile processing technicians to provide proper care and handling, with a corresponding reduction in cost of replacing surgical instruments.

DETAILED DESCRIPTION OF THE INVENTION

While the following description details the preferred embodiments of the present invention, it is to be understood that the invention is not limited in its application to the details of construction and arrangement of the parts illustrated in the accompanying figures, since the invention is capable of other embodiments and of being practiced in various ways.

Figure 1:
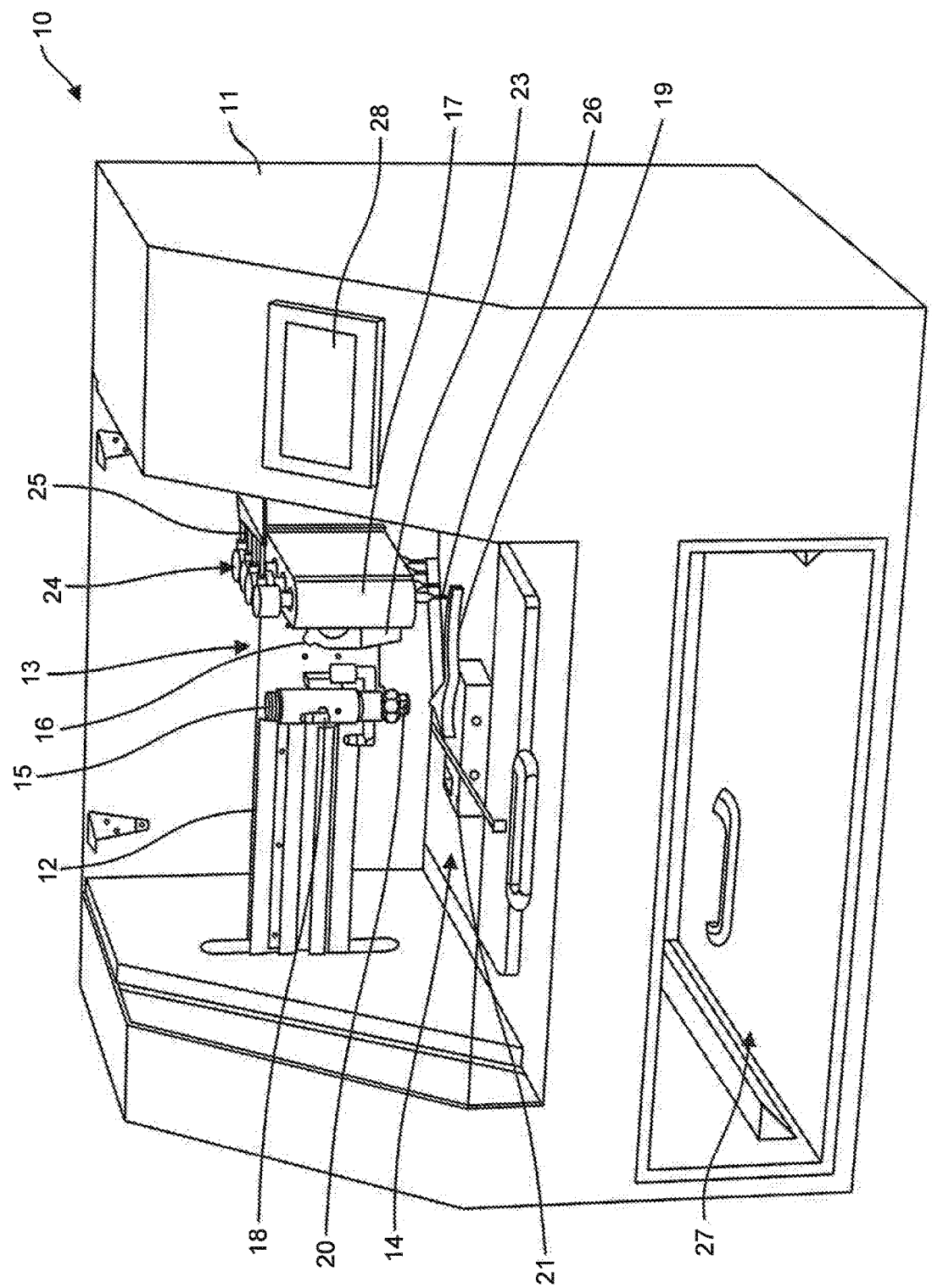
FIG. 1 shows a front, right side, perspective view of a robotic 3-D colored compound dispensing apparatus of the present invention.

FIG. 1 shows a front, right side, perspective view of a robotic 3-D colored dot dispensing apparatus 10 of the present invention. The dispensing apparatus 10 has a housing 11, a horizontal track 12 which moves a dispensing head system 13 along a horizontal X-axis and along a vertical Z-axis, and a work piece support table 14 which moves along a horizontal Y-axis perpendicular to the X-axis (see FIG. 2). The dispensing head system has a surface activator dispensing head 15, a flash off blower 16, and a colored compound dispensing head 17. The surface activator dispensing head 15 has an air feed port 18 to generate a spray of surface activator on the surface of a work piece, such as a metal medical instrument 19, through a nozzle 20. The medical instrument 19 shown in FIG. 1 is a rongeur positioned on the work piece support table 14 beneath a nozzle 20 of the surface activator dispensing head 15. The instrument 19 is shown positioned on an instrument holder 21. The flash off blower 16 has an air directioner 23. The colored compound dispensing head 17 has cartridges 24 filled with colored compound and air feed ports 25 to dispense the colored compound from the cartridges 24 through nozzles 26. The housing 11 has a heat curing oven 27 for the instrument 19 to harden the colored compound after it has been printed onto the surface of the instrument 19. The housing 11 contains a programmable processor and controller for activating the dispensing head system 13, the work piece support table 14, the surface activator dispensing head 15, the flash off blower 16, and the colored compound dispensing head 17. The processor and controller produce the activating steps at the desired times, with the desired positions, and with the desired sequences. A user can program the desired activating steps through a control touch screen 28 by methods well known in the art.

Figure 2:
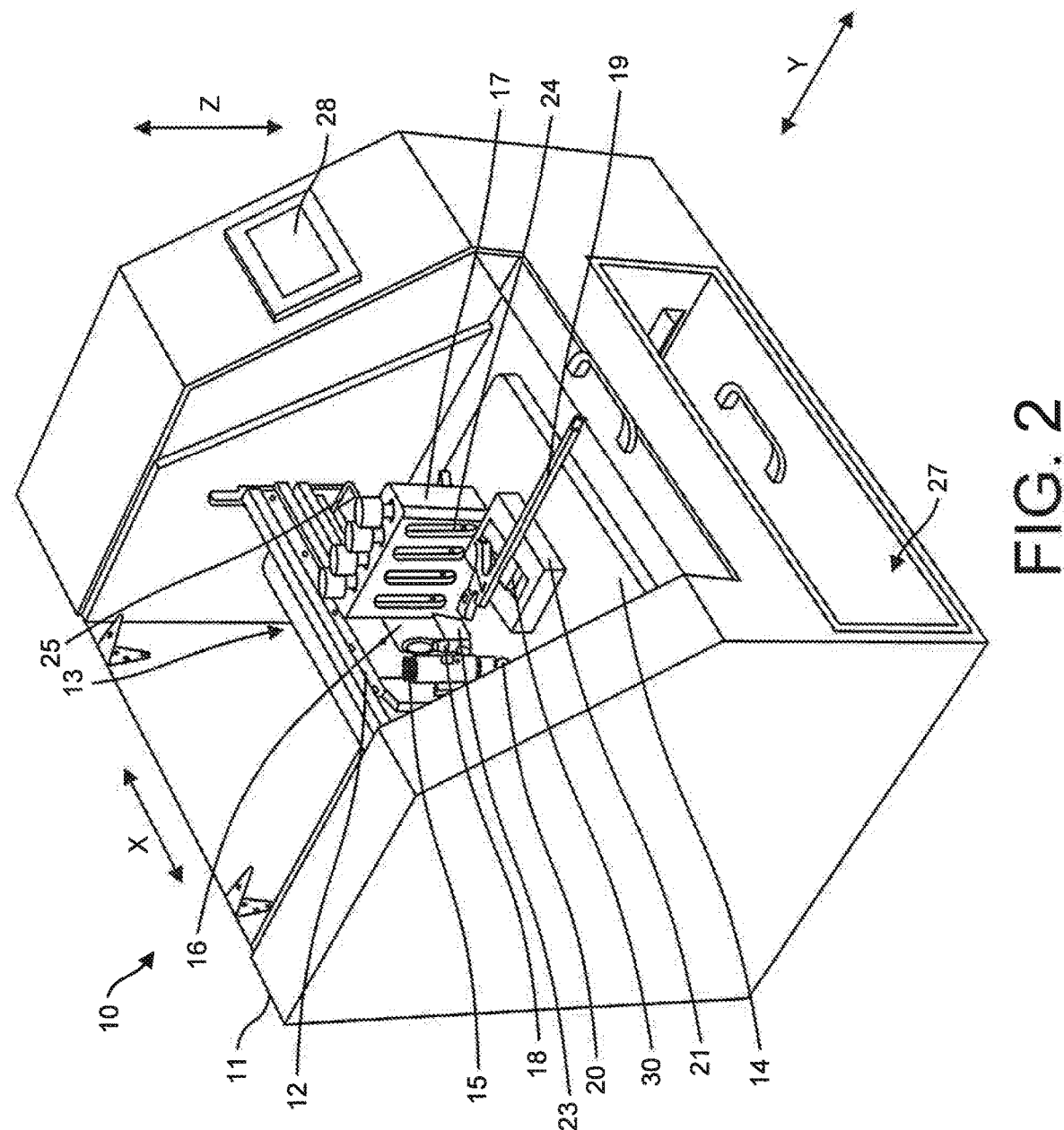
FIG. 2 shows a front, top, left side perspective view of the robotic 3-D colored compound dispensing apparatus.
Figure 3:
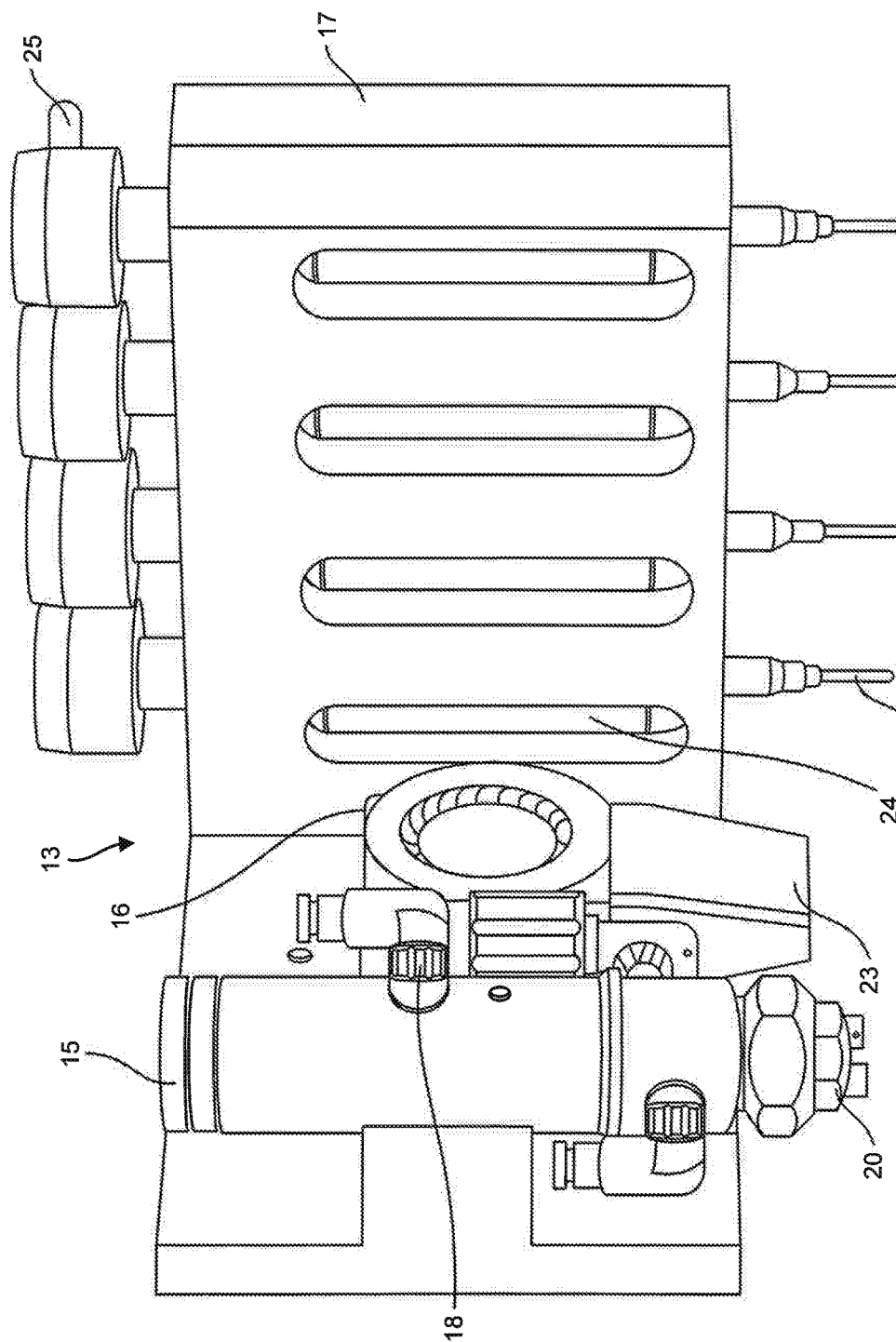
FIG. 3 shows an enlarged side perspective view of the dispensing head system.
Figure 4:
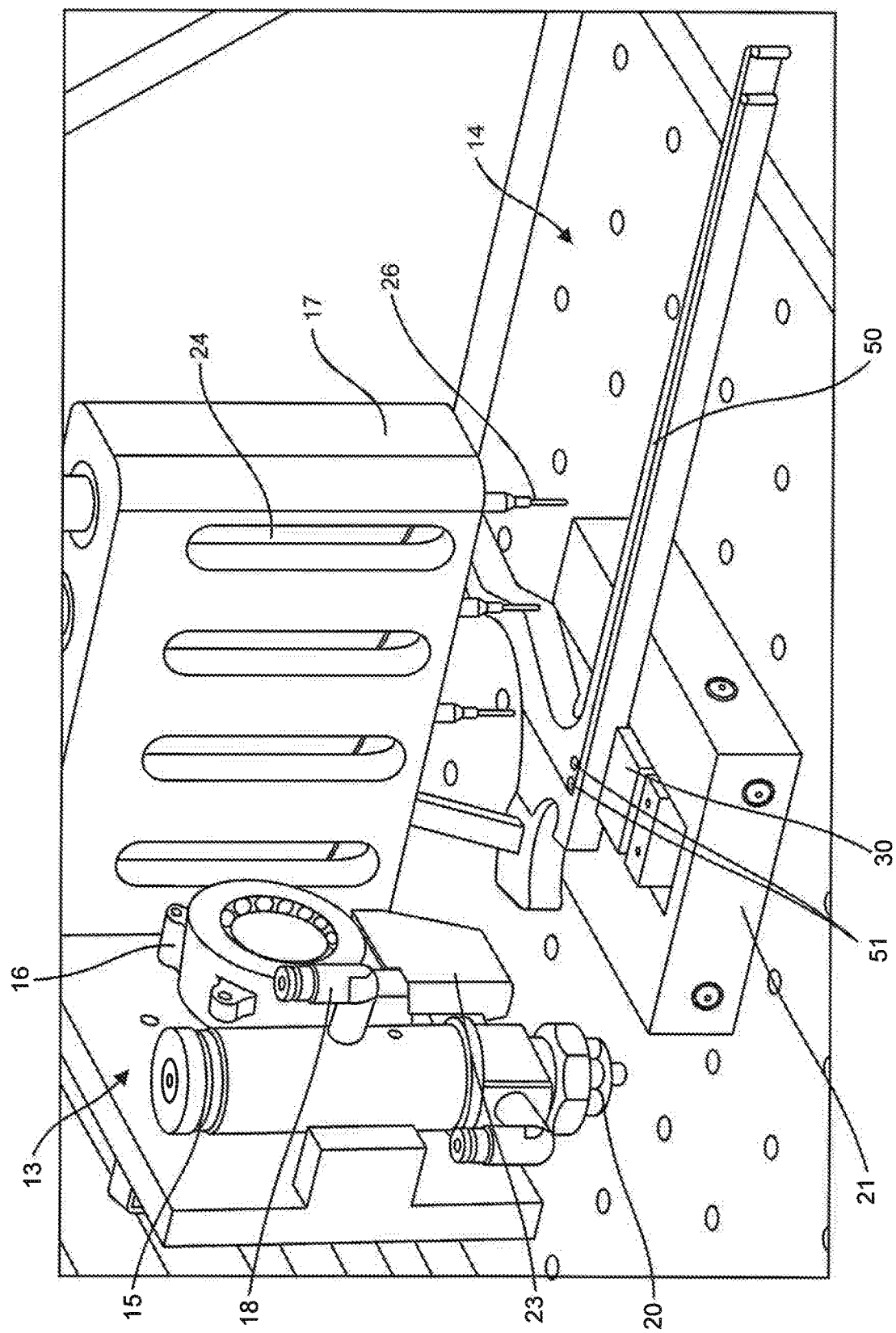
FIG. 4 shows an enlarged side perspective view of the dispensing head system, further showing a colored compound dispensing head positioned over an instrument.

FIG. 2 shows a front, top, left side perspective view of the robotic 3-D colored dot dispensing apparatus 10. FIG. 2 further shows and instrument holder 21 with a clamping mechanism 30 to hold an instrument 19 in place. The directions of the X, Y, and Z axes are shown by the double arrows labeled X, Y, and Z. FIG. 3 shows an enlarged side perspective view of the dispensing head system 13. FIG. 4 shows an enlarged side perspective view of the dispensing head system 13, further showing the colored compound dispensing head 17 positioned over an instrument which is a rongeur 50. Dots 51 are shown on the rongeur 50 and range, preferably, from 2 to 5 mm in diameter.

Figure 5:
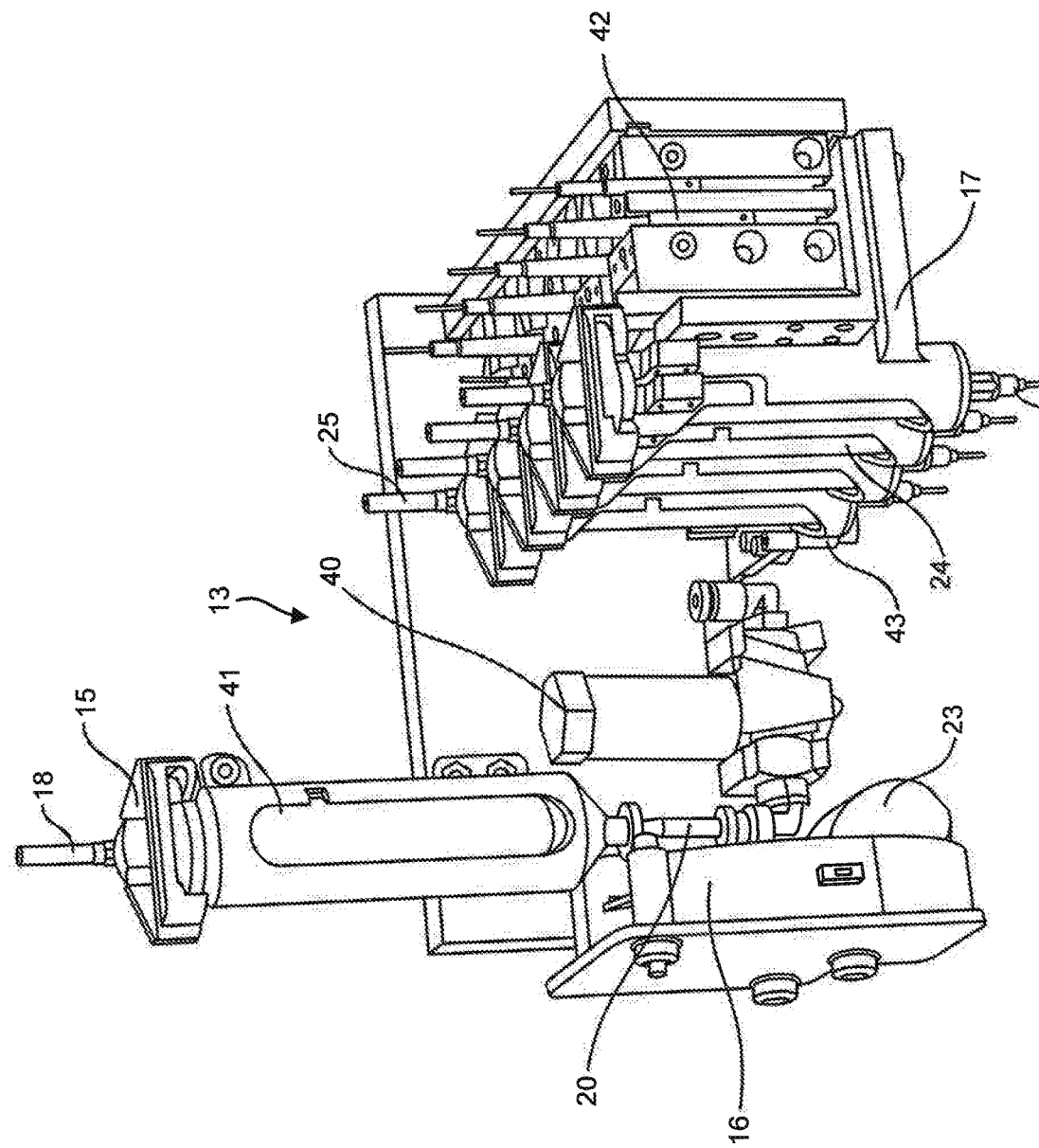
FIG. 5 shows an enlarged front, top perspective view of a dispensing head system, further showing a spray nozzle attached to a surface activator dispensing head.

FIG. 5 shows an enlarged front, top perspective view of the dispensing head system 13, further showing an ExAir spray nozzle 40 (EXAIR, Cincinnati, Ohio) attached to the nozzle 20 of the surface activator dispensing head 15. The surface activator spray head 15 can use cartridges 41 to contain the surface activating agent. The flash off blower 16 is positioned on the opposite side of the surface activator dispensing head 15 to accommodate the ExAir spray nozzle 40. FIG. 5 further shows microactuators 42 (for example, Northwest UAV, McMinnville, Oreg.) connected to the colored compound head dispensing cartridges 24. The microactuators 42 raise and lower the cartridges 24 up and down along the Z-axis. Associated with the microactuators 42 is a height sensor 43 to monitor the height of the colored compound dispensing head cartridge nozzles 26 above the surface of an instrument 19. Signals from the height sensor 43 allow accurate positioning of the nozzles 26 above the surface of the instrument 19 for printing the colored dot on to the instrument 19 surface.

The robotic 3-D colored dot dispensing apparatus can be sized similar to a desk top laser printer with approximate dimensions of 20"×16"×12". The colored coding process of bonding colored dots of thermoset resin permanently on a metal surface can be automated in a way that is robust, repeatable and reliable, especially for the surface of stainless steel surgical instruments. The colored compound dispensing apparatus is easy to assemble and is universally capable of being used with a majority of handheld surgical instruments.

The colored coating of the present invention is composed of one or more thermoset resin colored spots or dots printed or deposited on a metal surface. The thermoset resin is a liquid, one component, heat curing thermoset polymer adhesive, such as Master Bond Supreme 10HT (Masterbond, Hackensack, N.J.) and is, preferably, a bis-phenol A thermoset. The thermoset resin thermoset is colored with a heat resistant colored pigment, for example, a Ferro pigment (Ferro Corporation, Mayfield Heights, Ohio) of any desired color. The colored pigment is mixed with the liquid thermoset resin in the amount of 1% to 3%, w/w, w/v, or v/v, forming a uniform mixture of heat curing thermoset resin plus colored pigment.

In order for the colored thermoset resin to bond adequately to a metal surface the metal surface must first be pretreated with a surface activating agent. A preferred activating agent is gamma-glycidoxypropyltrimethoxysilane (www.sigmaaldrich.com). Once the surface is activated one or more liquid colored thermoset resin spots, marks, or dots are placed on a metal surface of an instrument or other object. A sequence of colored dots can be used as a code to identify the instrument. The instrument with the liquid colored thermoset resin dots is placed in an oven and heated at a temperature and duration pre-set by the apparatus controls providing an ideal heat and time cycle assuring consistency of the thermoset resin. The liquid colored thermoset resin hardens permanently and remains fixed on the instrument permanently.

Figure 6:
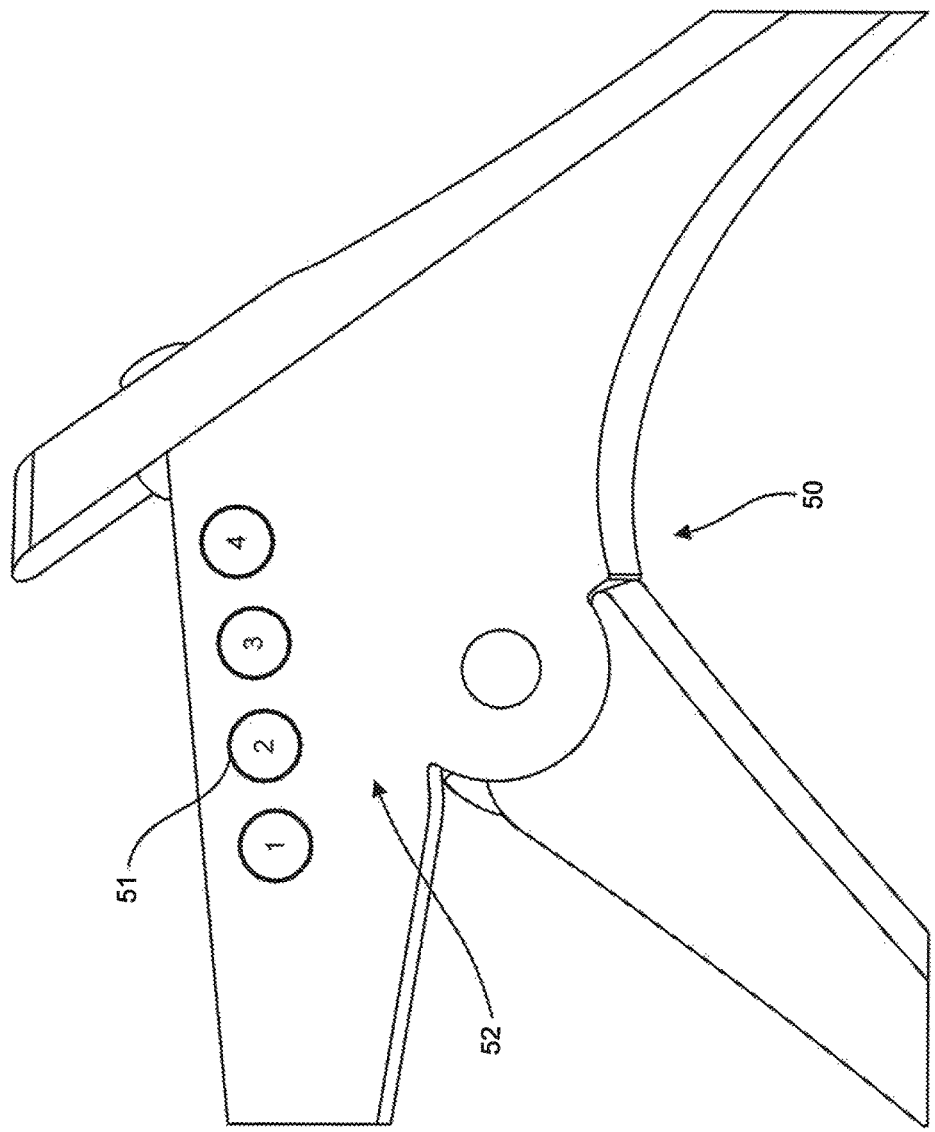
FIG. 6 is a side view illustration of a portion of a handle of a rongeur having four colored thermoset resin dots on a surface of the rongeur.

FIG. 6 is a side view illustration of a portion of a handle of a rongeur 50 having four dots 51 on a surface 52 of the rongeur 50. Each dot 51 may have a different color, represented by the numbers 1, 2, 3, and 4. The colored dots 51 are permanent, easily visible and easily distinguishable. Any colors can be used such as green, yellow, blue, pink, orange, purple, red, grey, and the like. Colored thermoset resin dots 51 can be read from left to right, with a larger dot on the left end of the line of dots indicating a first dot. The thermoset resin dots are resistant to steam and dry autoclaving, chemicals (water, sulfuric acid, ammonia, and methanol), scratching, and wear. They are biocompatible, noncytotoxic, and do not support bacterial growth. The colored thermoset resin dots withstand abrasion, traditional hospital cleaning chemicals, corrosion, and vibrations. The process of applying the colored thermoset resin to the surface of the instrument and heat curing the thermoset resin does not impair instrument integrity or function. The heat cured thermoset resin dots are heat resistant up to 204 degrees C., have a sheer strength on steel of 2000 PSI, and maximum elongation of 6.1%.

The method of using the robotic 3-D colored compound dispensing apparatus 10 of the present invention is described as follows.

Step 1: A user loads or replaces color cartridges 24 as needed in the colored compound dispensing head 17 and fills the surface activator dispensing head 15 with surface activator fluid.

Step 2: The user enters the desired color code sequence desired for the instruments in the control touch screen 28 and enters a size (small, medium, large) for each dot 51. A first dot being the farthest left can be slightly larger to indicate reading direction.

Step 3: The support table 14 is fully extended outwards and the user places one or more instruments at a pre-set location onto universal instrument holders 21, aligning and orienting the instrument where colored dots will be applied. A laser indicator may be used to aid the user in manually aligning and positioning the instrument. The user then presses a RUN function.

Step 4: The support table 14 moves in the Y-axis direction locating the instrument in depth. The surface activator dispensing head 15 moves along the X-axis, positioning the dispensing nozzle 20 over the instrument. A surface activating agent is sprayed onto a surface 52 of the instrument. Thereafter, the flash off blower 16 aids in the flash evaporation of the surface activating agent.

Step 5: The colored compound dispensing head 17 moves along the X-axis direction, locating the color cartridges 24 in position. The height sensor 43 is deployed and the colored compound dispensing head 17 moves downwards towards the instrument surface 52 until the height sensor 43 touches the surface 52, setting the proper height distance between the colored compound dispensing nozzles 26 and the surface 52. The height sensor 43 then is then retracted.

Step 6: The support table 14 moves along the y-axis direction, locating the desired first color position, based on the color sequence entered by the user through the control touch screen 28. The microactuator 42 advances a first color cartridge 24 downwards towards the instrument surface 52 a measured distance, based on the height sensor 43 output, and the color compound is dispensed onto the instrument surface to create the first colored dot 51. The microactuator 42 is then retracted.

Step 7: The support table then moves to second, third, and fourth programmed positions for creating the second, third, and fourth colored dots, repeating steps 4 through 6.

Step 8: Thereafter, instruments are removed and placed in a tray and subsequently placed in the heat curing oven 27 for a programmed curing process of the colored thermoset resin colored dots.

This entire sequence of Steps 1-7 can be programmed by the user to be automatically executed with a single command (1-Click). The support table can have pre-set positions for multiple instruments to be color coded in sequence in a single cycle of operation.

The colored thermoset resin dots will not flake, peel, turn up at the edges, thus preventing color coding material from falling into a patient's thoracic or peritoneal cavity or harbor bacteria. A routinely sterilized or repaired instrument can be immediately identified and put in the surgical set so it is available for a surgeon's next case. Unidentified instruments that usually end up in the graveyard can be eliminated. Coding with the colored thermoset resin dots provide for surgeons being held accountable for instruments assigned to them which results in decreased costs associated with instruments being used incorrectly or inappropriately. Each surgeon can have his or her own color coding. The color coding system of the present invention can be applied to other surgical equipment such as rigid scopes, surgical drills, specialty instruments and the like used in the operating room.

There is chemical bonding between the metal surface and the colored polymer by the action of the activating agent to form a composition of metal and colored polymer. The silane solution works as a chemical bonding agent creating an anchor between the metal surface and the polymer compound (iron-silane-bisphenol A). Specifically, the chemical bonding forms an iron-bis-phenol A colored thermoset resin compound which accounts for the strong adhesion of the colored thermoset resin dot on the surface of the metal. The present method produces a product consisting of iron, his-phenol A thermoset resin, and colored pigment.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, any desired number of colored thermoset resin dots of the present invention can be bonded to the metal surface of surgical instruments and other metal surfaces. The colored thermoset resin dots can be any desired size and shape. Any suitable colored pigment may be used to color the thermoset resin. The process can be used to bond any colored liquid thermoset resin on to any metal surface in addition to iron-based surfaces.

It will be understood that various changes in the details, materials, and arrangements of the parts which have been described and illustrated above in order to explain the nature of this invention may be made by those skilled in the art without departing from the principle and scope of the invention as recited in the following claims.

We claim:

1. A method of depositing colored thermoset resin dots on a metal surface for color coding, comprising:
   1) combining a liquid one component thermoset resin with a colored pigment to form a 1% to 3% concentration of the colored pigment in the liquid one component thermoset resin, w/w, w/v, v/v to form a colored liquid thermoset resin;

2) treating the metal surface with a surface activating agent;

3) evaporating the surface activating agent on the metal surface to form an activated metal surface;

4) depositing the mixture of colored liquid thermoset resin on the activated metal surface; and 5) curing the colored liquid thermoset resin on the activated metal surface by heating the colored liquid thermoset resin, wherein the surface activating agent is gamma-glycidopropyl-trimethoxysilane.

2. The method of claim 1, wherein the liquid one component thermoset resin is a heat curing, bis-phenol A thermoset resin.

3. The method of claim 1, wherein the method is performed with a 3-D colored dot printing apparatus for color coding, comprising:

a) a track which moves a dispensing head system horizontally and vertically in X and Z directions, respectively;

b) a support table for one or more workpieces which moves in a horizontal Y direction, perpendicular to the X direction;

c) the dispensing head having a surface activator dispensing head and a colored compound dispensing head;

d) a programmable processor/controller which drives the dispensing head system and activates the surface activator dispensing head and the colored compound dispensing head to deposit and bond one or more colored dots to a metal surface of an instrument;

e) an air pressure source for the surface activator dispensing head and for the colored compound dispensing head; and f) the colored compound dispensing head having one or more microactuators to raise and lower the colored compound dispensing head in the Z direction and a height sensor to position the colored compound dispensing head above the metal surface of the instrument.

* * * * *